United States Patent
Singh et al.

(10) Patent No.: US 11,478,212 B2
(45) Date of Patent: Oct. 25, 2022

(54) METHOD FOR CONTROLLING SCANNER BY ESTIMATING PATIENT INTERNAL ANATOMICAL STRUCTURES FROM SURFACE DATA USING BODY-SURFACE AND ORGAN-SURFACE LATENT VARIABLES

(71) Applicant: Siemens Healthcare GmbH, Erlangen (DE)

(72) Inventors: Vivek Kumar Singh, Princeton, NJ (US); Andreas Krauss, Bubenreuth (DE); Birgi Tamersoy, Erlangen (DE); Terrence Chen, Princeton, NJ (US); Kai Ma, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 313 days.

(21) Appl. No.: 15/883,328

(22) Filed: Jan. 30, 2018

(65) Prior Publication Data
US 2018/0228460 A1    Aug. 16, 2018

Related U.S. Application Data

(60) Provisional application No. 62/459,651, filed on Feb. 16, 2017.

(51) Int. Cl.
*A61B 6/00* (2006.01)
*A61B 5/00* (2006.01)
(Continued)

(52) U.S. Cl.
CPC ............ *A61B 6/545* (2013.01); *A61B 5/0035* (2013.01); *A61B 5/0064* (2013.01); *A61B 5/055* (2013.01);
(Continued)

(58) Field of Classification Search
CPC ..... A61B 6/545; A61B 5/0035; A61B 6/5217; A61B 5/0555; A61B 6/542; A61B 5/0064;
(Continued)

(56) References Cited

U.S. PATENT DOCUMENTS

| 9,373,087 B2 * | 6/2016 | Nowozin | G06N 20/00 |
| 2007/0238963 A1 * | 10/2007 | Kaminaga | A61B 6/032 600/407 |

(Continued)

FOREIGN PATENT DOCUMENTS

| CN | 1802122 A | 7/2006 |
| CN | 101167105 A | 4/2008 |

(Continued)

OTHER PUBLICATIONS

H. Suk, S. Lee, & D. Shen. Latent feature representation with stacked auto-encoder for AD/MCI diagnosis. Brain Struct Funct 220, 841-859 (2015). https://doi.org/10.1007/s00429-013-0687-3. (Year: 2015).*

(Continued)

*Primary Examiner* — Christopher Koharski
*Assistant Examiner* — Richmond J Van Winter

(57) ABSTRACT

A method for controlling a scanner comprises: sensing an outer surface of a body of a subject to collect body surface data, using machine learning to predict a surface of an internal organ of the subject based on the body surface data, and controlling the scanner based on the predicted surface of the internal organ.

10 Claims, 14 Drawing Sheets

(51) Int. Cl.
*A61B 5/055* (2006.01)
*A61B 5/107* (2006.01)
*A61B 6/03* (2006.01)
*G01R 33/54* (2006.01)
*G01R 33/56* (2006.01)
*G06T 7/12* (2017.01)
*G01R 33/28* (2006.01)

(52) U.S. Cl.
CPC .......... *A61B 5/1077* (2013.01); *A61B 5/7267* (2013.01); *A61B 5/7278* (2013.01); *A61B 6/032* (2013.01); *A61B 6/5217* (2013.01); *A61B 6/542* (2013.01); *G01R 33/543* (2013.01); *G01R 33/5608* (2013.01); *G06T 7/12* (2017.01); *A61B 2560/029* (2013.01); *A61B 2576/00* (2013.01); *G01R 33/283* (2013.01)

(58) Field of Classification Search
CPC ..... A61B 5/7267; A61B 5/7278; A61B 5/055; A61B 6/032; A61B 5/1077; A61B 2576/00; A61B 2560/029; A61B 5/7225; A61B 5/0077; A61B 5/1079; G01R 33/5608; G01R 33/543; G01R 33/283; G06T 7/12; G06T 2207/20084; G16H 50/30; G16H 50/70; G06N 20/00
See application file for complete search history.

(56) References Cited

U.S. PATENT DOCUMENTS

| | | | | |
|---|---|---|---|---|
| 2008/0154565 | A1* | 6/2008 | Florin | G06K 9/6256 703/11 |
| 2009/0285357 | A1* | 11/2009 | Khamene | A61B 6/5217 378/20 |
| 2011/0044521 | A1 | 2/2011 | Tewfik et al. | |
| 2011/0110572 | A1* | 5/2011 | Guehring | A61B 6/545 382/131 |
| 2016/0236009 | A1* | 8/2016 | Sabczynski | A61N 5/1037 |
| 2016/0260213 | A1* | 9/2016 | Reda | G06T 19/20 |
| 2016/0306924 | A1 | 10/2016 | Singh et al. | |
| 2017/0100078 | A1* | 4/2017 | Han | A61B 5/7278 |
| 2018/0228460 | A1 | 8/2018 | Singh et al. | |
| 2019/0018149 | A1* | 1/2019 | Traub | A61N 5/1048 |

FOREIGN PATENT DOCUMENTS

| | | | | |
|---|---|---|---|---|
| CN | 102388403 | A | 3/2012 | |
| CN | 102631195 | A | 8/2012 | |
| CN | 104545906 | A | 4/2015 | |
| CN | 105997093 | A | 10/2016 | |
| CN | 106157295 | A | 11/2016 | |
| EP | 2462560 | B1 | 10/2018 | |
| EP | 3537976 | A1 * | 9/2019 | .......... A61B 5/0077 |
| WO | 2008063494 | A3 | 8/2008 | |
| WO | 2012151498 | A3 | 1/2013 | |
| WO | 2015055485 | A1 | 4/2015 | |
| WO | WO-2015055485 | A1 * | 4/2015 | .......... A61N 5/1049 |
| WO | 2016073841 | A1 | 5/2016 | |

OTHER PUBLICATIONS

H. Shin, M. Orton, D. Collins, S. Doran, & M. Leach. Stacked Autoencoders for Unsupervised Feature Learning and Multiple Organ Detection in a Pilot Study Using 4D Patient Data. IEEE. Transactions on Pattern Analysis and Machine Intelligence 35, No. 8, 1930-1943 (2013). doi: 10.1109/TPAMI.2012.277. (Year: 2013).*
V. Singh, Y. Chang, K. Ma, M. Wels, G. Soza, & T. Chen. Estimating a Patient Surface Model for Optimizing the Medical Scanning Workflow. 472-479; 2014; Springer International Publishing Switzerland 2014. (Year: 2014).*
Fayad, Hadi et al. "Technical note: Correlation of respiratory motion between external patient surface and internal anatomical landmarks" Medical Physics, Jun. 2011, 38(6), pp. 3157-3164.
https://en.wikipedia.org/wiki/Inpainting, Nov. 2017.
Liepe, Juliane, et al. "Accurate reconstruction of cell and particle tracks from 3D live imaging data" Cell systems 3.1 (2016): 102-107.
Cui, Xueli. "Respiratory Motion modeling Based on 4D Lung CT Image." China Master's Theses (2014): 1138-937.
Roweis, et al., "Nonlinear Dimensionality Reduction by Locally Linear Embedding"; Science Magazine, vol. 290, Dec. 22, 2000; www.sciencemag.org; pp. 2323-2326.
Singh V. et. al.; "Estimating a Patient Surface Model for Optimizing the Medical Scanning Workflow"; p. 472-479; 2014; Springer International Publishing Switzerland 2014.
S. Bauer, et al., "Multi-modal Surface Registration for Markerless Initial Patient Setup in Radiation Therapy Using Microsoft's Kinect Sensor," IEEE International Conference on Computer Vision Workshops (ICCV Workshops), pp. 1175-1181, 2011.

* cited by examiner

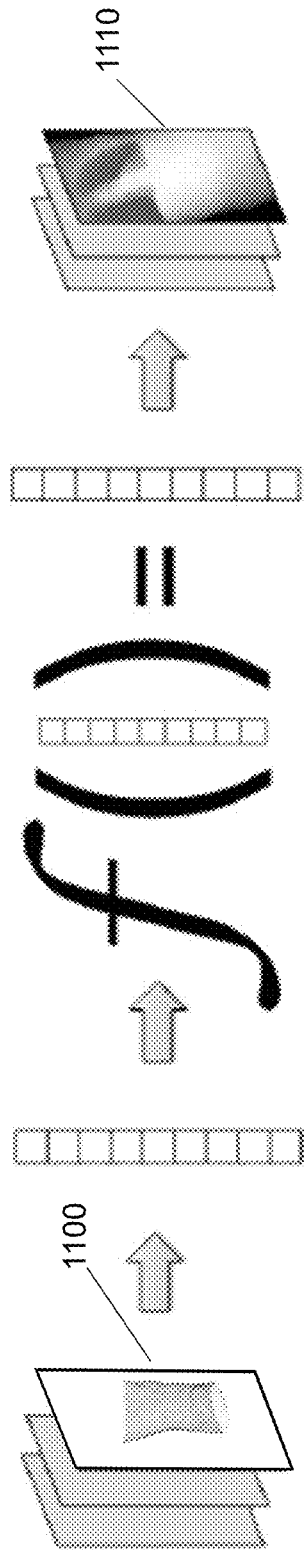
FIG. 11
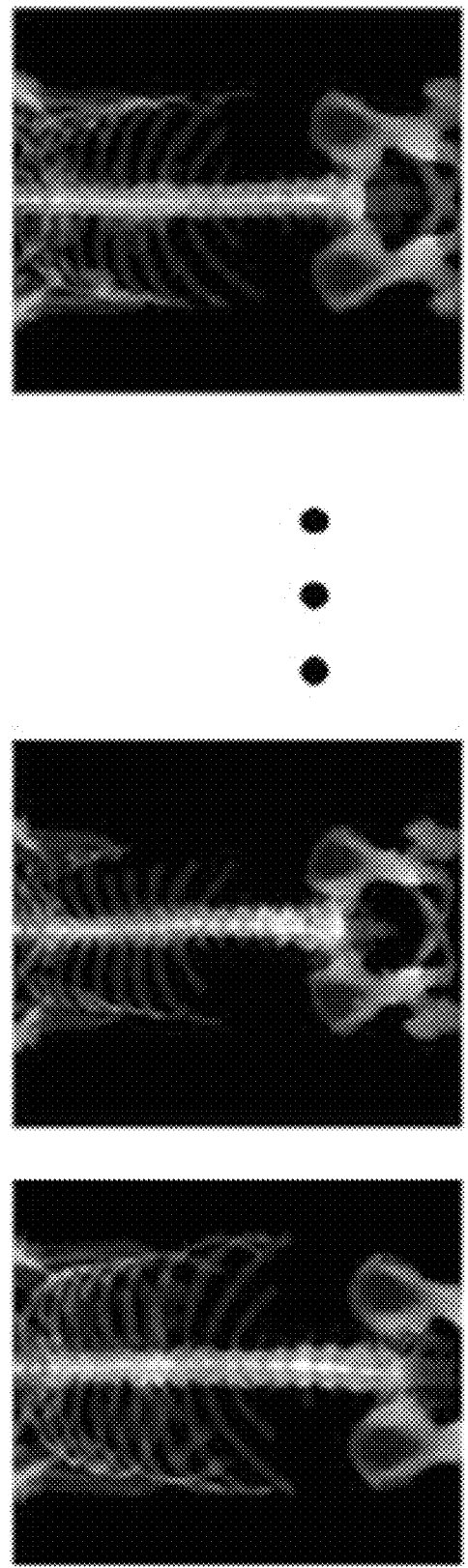
FIG. 12A
FIG. 12B
FIG. 12C

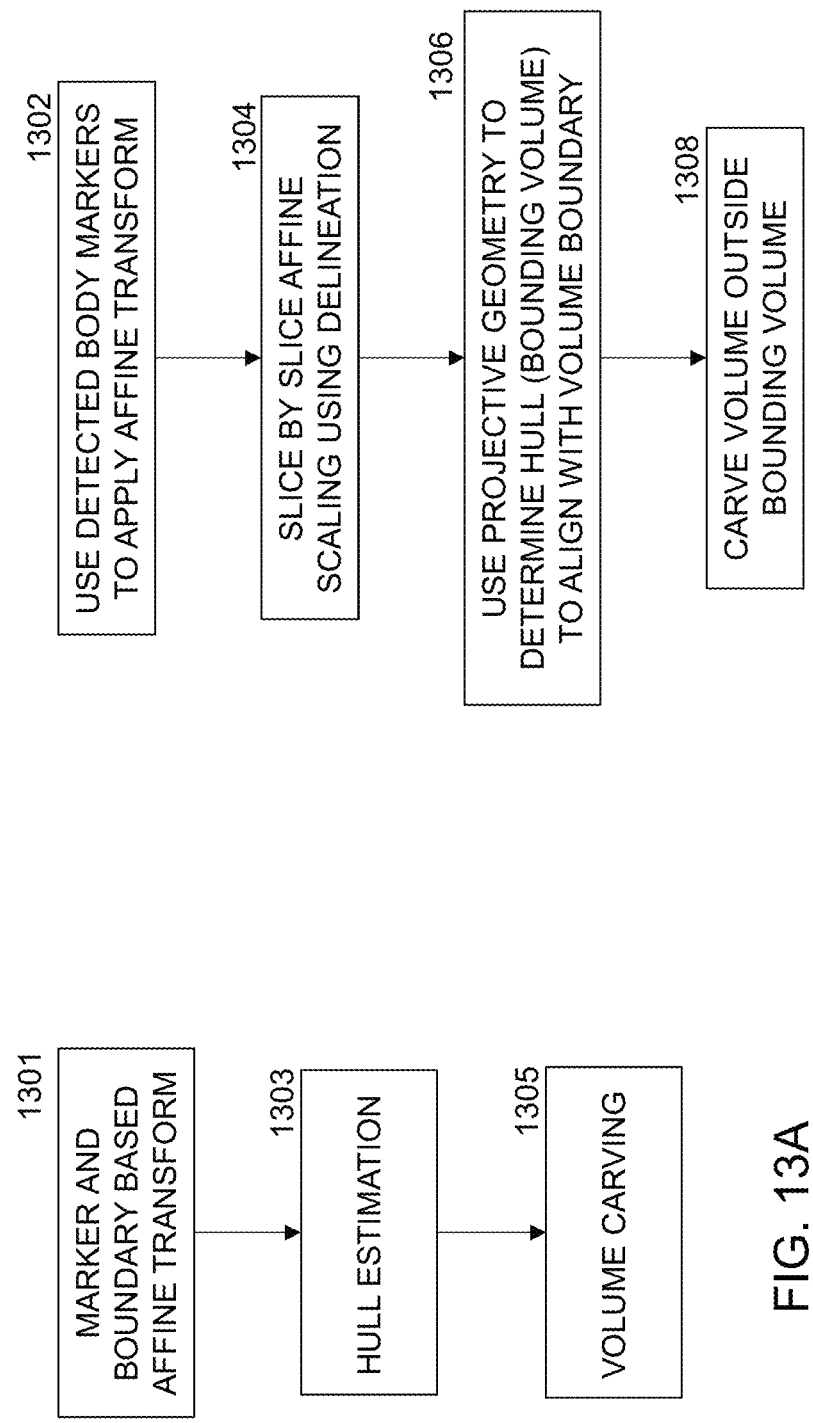

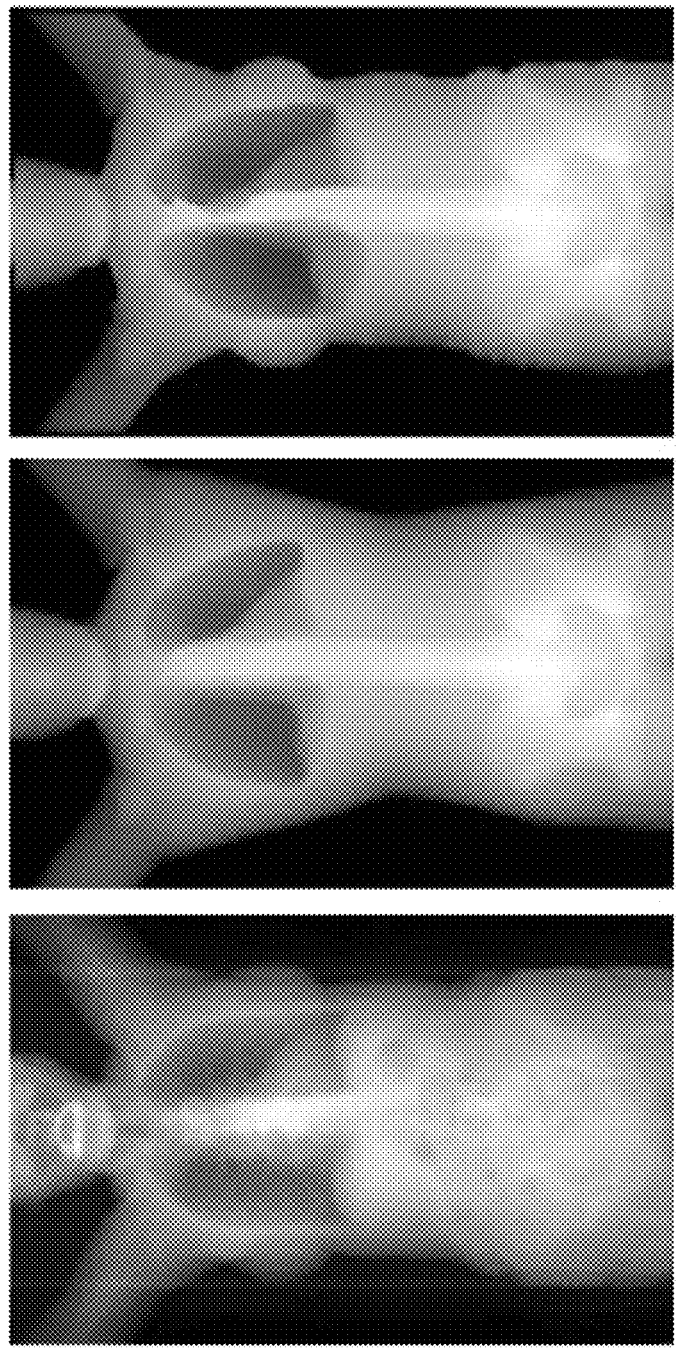

METHOD FOR CONTROLLING SCANNER BY ESTIMATING PATIENT INTERNAL ANATOMICAL STRUCTURES FROM SURFACE DATA USING BODY-SURFACE AND ORGAN-SURFACE LATENT VARIABLES

CROSS REFERENCE

This application claims priority to U.S. Provisional Application No. 62/459,651 filed on Feb. 16, 2017, the contents of which are hereby incorporated by reference.

FIELD

This disclosure relates generally to medical imaging systems, and more specifically to controls for imaging scanners.

BACKGROUND

To reduce unnecessary radiation, medical scanning equipment should limit the regions of the patient that are scanned. Because of the variation in patient body shapes, body sizes, clothing, and the like, a technician operating a medical imaging scanner may be faced with the difficult task of trying to determine, roughly, the hidden location of an internal organ or region of interest in a patient. The location of an internal organ can be determined by the technician from low-dose topogram images, which result in extra radiation of the patients. The technician then manually positions the patient such that the region of interest is optimally positioned with respect to the scanner. The manual patient positioning process is time-consuming and costly.

SUMMARY

In some embodiments, a method for controlling a scanner comprises: sensing an outer surface of a body of a subject to collect body surface data; using machine learning to predict a surface of an internal organ of the subject based on the body surface data; and controlling the scanner based on the predicted surface of the internal organ.

In some embodiments, a system for controlling a scanner comprises: a depth sensor for sensing an outer surface of a body of a subject to collect body surface data; a processor coupled to the scanner; and a non-transitory, machine readable storage medium coupled to the processor and encoded with program instructions for: using machine learning to predict a surface of an internal organ of the subject based on the body surface data; and controlling the scanner based on the predicted surface of the internal organ.

In some embodiments, a non-transitory, machine readable storage medium encoded with program instructions for controlling a scanner, such that when a processor executes the program instructions, the processor performs a method comprising: receiving body surface data representing an outer surface of a body of a subject from a depth sensor; using machine learning to predict a surface of an internal organ of the subject based on the body surface data; and controlling the scanner based on the predicted surface of the internal organ.

BRIEF DESCRIPTION OF THE DRAWINGS

FIG. 11 is representation of a volumetric regression to obtain organ or bone masks from the skin surface.

FIG. 12A-12C show cropped normalized volumes suitable for bone mask regression.

FIGS. 13A and 13B are flow charts showing a method for topogram based synthetic CT refinement.

FIGS. 14A-14C show an original CT image, the corresponding synthetic CT result using volumetric regression, and results after refinement using the topogram image, respectively.

DETAILED DESCRIPTION

Figure 1:
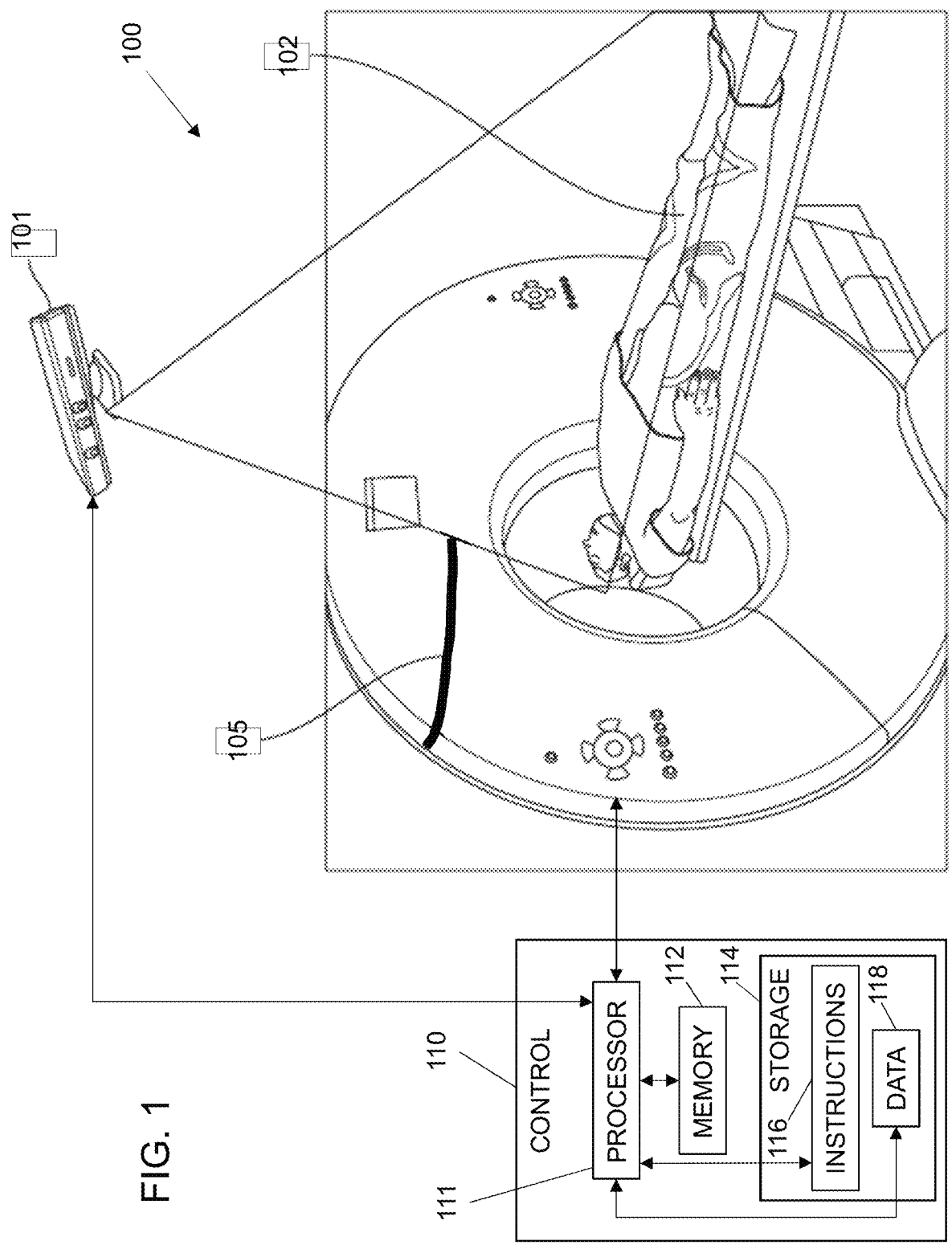
FIG. 1 is a schematic diagram of a medical imaging system according to some embodiments.

This description of the exemplary embodiments is intended to be read in connection with the accompanying drawings, which are to be considered part of the entire written description.

This disclosure describes a medical imaging system, and a method, system, and non-transitory, machine-readable storage medium containing computer instructions for predicting the internal anatomy of the patient based on patient surface measurements, and controlling the medical imaging system based on the prediction. The predicted internal anatomy may include, but is not limited to, internal body markers such as lung center, thyroid, organ surfaces such as lung, heart, brain, etc.

In some embodiments, the surface measurements may be obtained using off-the-shelf 2.5D or 3D depth sensors. For example, medical imaging devices may be equipped with a 3D camera to observe the patient. The predicted locations of internal anatomical structures can be achieved by learning a statistical correlation model between the detailed patient surface geometry sensed by the 2.5D depth sensor and the internal anatomical structures (such as organs and body markers). The methods and devices can learn the correlation model using machine learning from a large dataset.

Some embodiments include a system to predict the locations of internal anatomical structures based on geometric measurements on the patient's body surface using machine learning algorithms. The predicted structures may include body markers (e.g., joints) and/or organ surfaces. The structures may be estimated within an error range based on correlation statistics in the training dataset. The estimation can be performed using a regressor 203 employing linear regression, sparse linear regression, or machine learning.

The system estimates the internal structures as a regression task. In computer vision, this literature can also be viewed as an "inpainting" problem, where the surface of the body is known and the system attempts to fill in missing internal details; in this scenario, a significant amount of data may be inpainted.

Some embodiments use machine learning techniques to learn a correlation model between the surface data and internal structures. This disclosure provides various regression methods such as sparse linear regression and non-linear deep regression.

In some embodiments, the surface data and internal structures may be represented as meshes (or points) or as volumetric masks. The regression methods can apply to surface data or volumetric data.

The ability to predict locations of certain internal anatomical structures provides several benefits when planning a medical scan, such as computed tomography (CT), magnetic resonance (MR), fluoroscopy or Ultrasound. For CT scanning, the predicted locations of internal anatomical structures can used to determine the scan range to obtain topogram or full CT scan, depending upon which organ will be scanned and how accurately the nearby structures can be predicted. The predicted locations of internal anatomical structures can also be useful to assist in coil placement for MR scanning. For ultrasound scanning, the predicted locations of internal anatomical structures may assist in the probe guidance by providing approximate position of the various organs. For fluoroscopy using dyna-CT scans, the predicted locations of internal anatomical structures can be useful for positioning as well.

In some embodiments, the system learns the spatial correlation of the instantaneous positions (of body surface and organ surface), which implicitly captures the motion correlation as well (determined by spatial correlation over multiple frames).

FIG. 1 shows a scanner system 100, including a control device 110 for controlling a scanner 105. The scanner 105 has a depth sensor 101 for sensing an outer surface 102 of a body of a subject to collect body surface data. The control device 110 has a processor 111 using machine learning to predict a surface of an internal organ 104 (FIG. 2) of the subject based on the body surface data 102. The processor 111 is configured (e.g., by software) for controlling the scanner 105 based on the predicted surface of the internal organ 104.

The scanner 105 can be an MR scanner, such as a "MAGNETOM VIDA"™ scanner, a CT scanner, such as a "SOMATOM CONFIDENCE RT Pro"™ CT Scanner, a PET scanner, such as the "BIOGRAPH HORIZON"™ PET/CT scanner, or an ultrasound scanner, such as the "ACUSON SC2000PRIME"™ cardiovascular ultrasound system, all sold by Siemens Medical Solutions USA, Inc. of Malvern, Pa. These are only examples, and other scanner makes and models may be used.

The scanner 105 is coupled to a control device 110, which can include an embedded processor 111, a computer, a microcontroller, an application specific integrated circuit (ASIC), a programmable gate array, or the like. The control device 110 includes a main memory 112, which can include a non-transitory, machine readable storage medium such as dynamic random access memory (DRAM). The secondary memory comprises a non-transitory, machine readable storage medium 114, such as a solid-state drive, hard disk drive (HDD) and/or removable storage drive, which can include a solid state memory, an optical disk drive, a flash drive, a magnetic tape drive, or the like. The non-transitory, machine readable storage medium 114 can include tangibly store therein computer software instructions 116 for causing the scanner 105 to perform various operations and data 118.

The surface measurements may be obtained using off-the-shelf 2.5D or 3D depth sensors 101 such as a "KINECT 2"™ 3 D camera sold by Microsoft Corporation of Redmond, Wash., "ASUS XTION"™ sold by AsusTeK Computer, Inc. of Taipei, TW), a stereo camera, or a time of flight camera (such as "SENZ3D" camera sold by Creative Technology Ltd of Singapore), or by 3D reconstructions from multiple 2D images. These sensors 101 are non-ionizing and are not known to pose any risk to the patient's health. The processor 111 of control device 110 sends commands to the scanner 105 and the 2.5D or 3D camera 101. The processor 111 receives RGB-D data from the 0.5D or 3D camera 101 and receives raw (MR, CT, PET or ultrasound) data from the scanner 105.

In some embodiments, a 3D avatar mesh of the subject is formed based on a 2.5D or 3D image from the depth camera, as disclosed in US 2015/0213646 A1 (application Ser. No. 14/604,829, filed Jan. 26, 2015), which is incorporated by reference herein in its entirety. A depth camera image of the subject is converted to a 3D point cloud. A plurality of anatomical landmarks are detected in the 3D point cloud. A 3D avatar mesh is initialized by aligning a template mesh to the 3D point cloud based on the detected anatomical landmarks. A personalized 3D avatar mesh of the subject is then generated by optimizing the 3D avatar mesh using a trained parametric deformable model (PDM).

Figure 2:
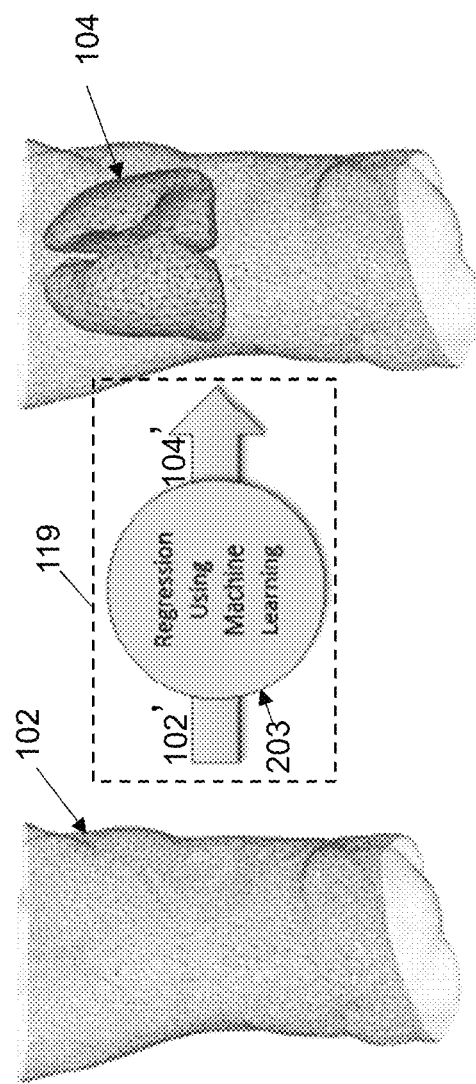
FIG. 2 is a schematic diagram of a method according to some embodiments.

FIG. 2 is a high-level schematic diagram of a method performed using the system 100 of FIG. 1. The method uses machine learning to predict an internal surface of an organ or body tissue, for controlling the scanner 105. The 2.5D or 3D sensor 101 captures a depth image (also referred to as an RGB-D image) of outer body surface 102 of the patient.

The control device 110 reduces the dimensionality of the body surface data 102 using manifold learning (e.g., principal component analysis, an autoencoder, or other machine learning method) to encode the body surface data into reduced dimensionality body surface data 102'.

The control device 110 has a prediction block 119 (including a regressor 203) for predicting a compact representation 104' of the surface of the internal organ 104 based on the reduced dimensionality body surface data 102'. In some embodiments, the prediction is performed by the prediction block 119 based on regression, using machine learning. The result of the prediction is a set 104' of principal coordinates or latent variables representing the surface of the internal organ 104. The control device 110 then performs a decoding process for expanding the compact representation 104' to reconstruct the organ surface data 104.

Figure 3A:
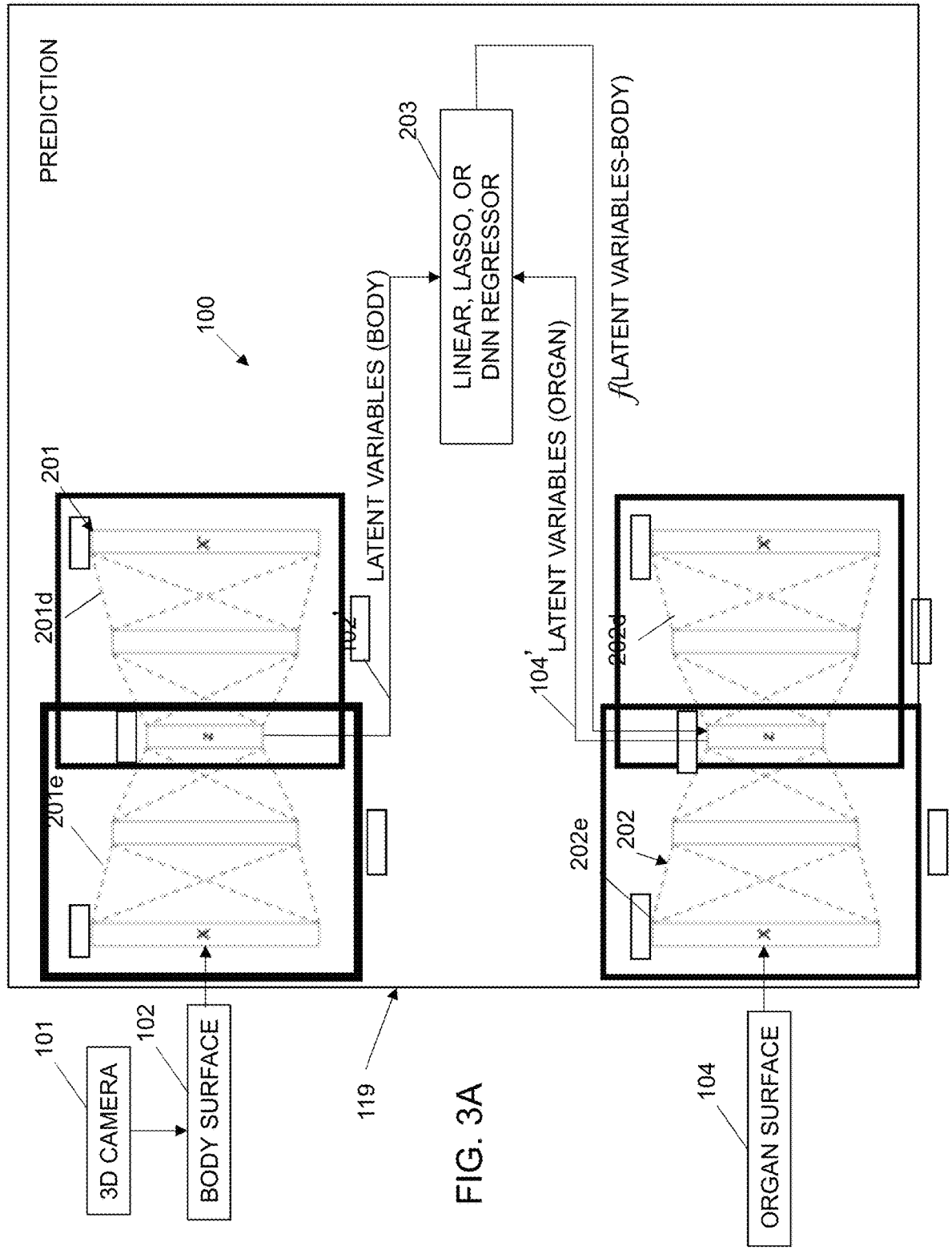
FIG. 3A is a block diagram of the scanning system of FIG. 1, configured for training.
Figure 3B:
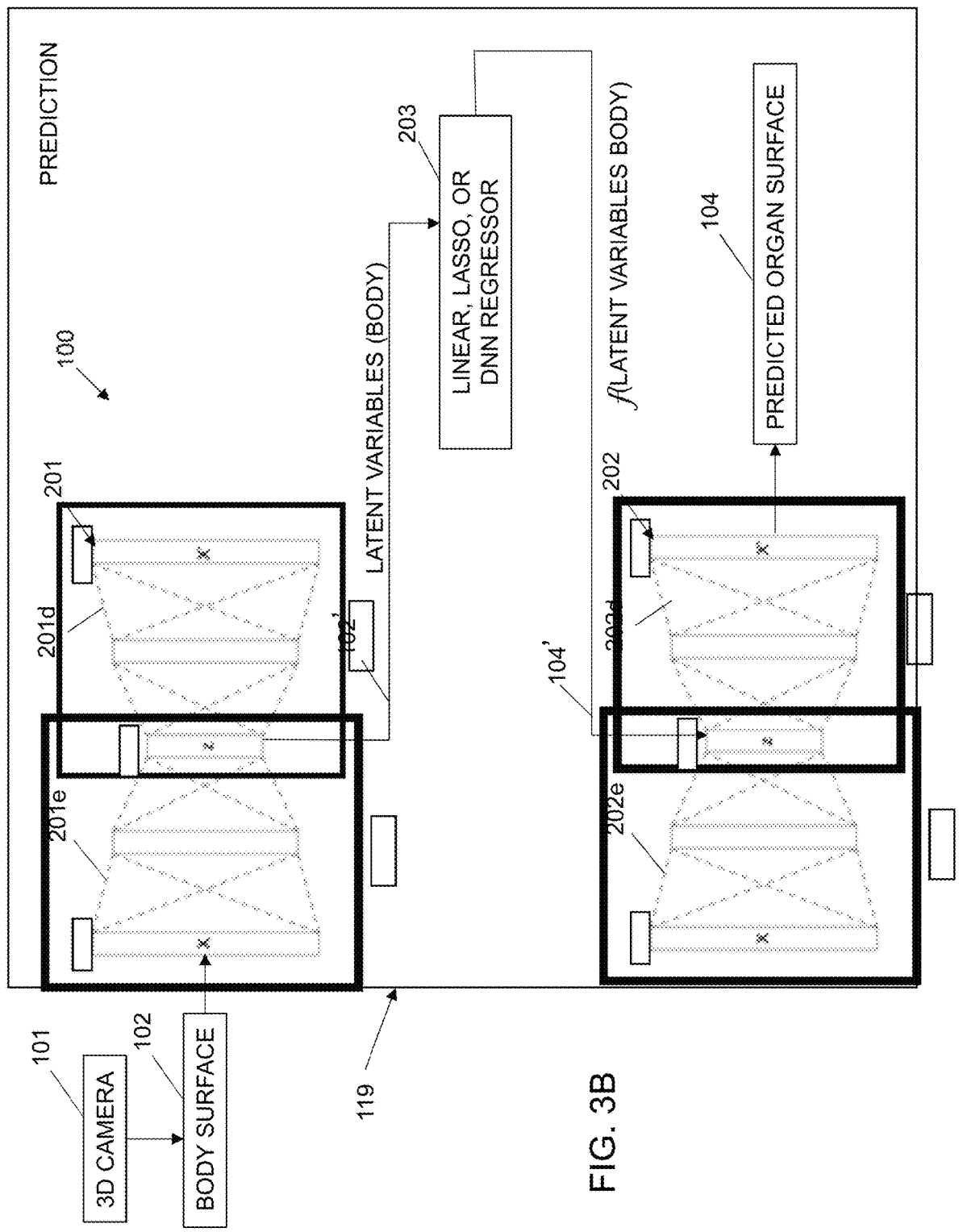
FIG. 3B is a block diagram of the scanning system of FIG. 3A configured for the test phase.

FIGS. 3A and 3B schematically show the apparatus and prediction block 119 of the system 100 of FIG. 2 in greater detail. The prediction block 119 can be implemented by the processor 111 executing instructions 116 stored in the control device 110, for example. FIGS. 3A and 3B show components 201-203 involved in predicting the organ surface data 104 based on body surface data 102. FIG. 3A shows the data flow during the training phase, and FIG. 3B shows the data flow during the test phase. In some embodiments, as shown in FIGS. 3A and 3B, a first autoencoder 201 performs dimensionality reduction. A regressor 203 determines a function $f$ for predicting the compact (latent variable or principal component) representation 104' of the organ surface 104 based on the compact (latent variable or principal component) representation 102' of the body surface 102. A second autoencoder 202 constructs the predicted organ surface data 104 based on the compact (latent variable or principal component) representation 104' of the organ surface 104.

With reference to FIG. 3A, the first autoencoder 201 is configured for reducing the dimensionality by encoding the body surface data 102 into body surface latent variables or principal components 102'. An autoencoder is an artificial neural network used for unsupervised machine learning. The autoencoder 201 learns a representation (encoding) for a set of data, for dimensionality reduction. The autoencoder 201 can be embodied as a feedforward, non-recurrent neural network having an encoder 201e with an input layer X, a decoder 201d with an output layer X' and one or more hidden layers Z connecting the input layer X and output layer X'. The autoencoder 201 is configured for reconstructing its own inputs (i.e., a body surface). When the autoencoder 201 has been trained sufficiently, the difference between the output X' and input X is smaller than a threshold value. The data representation at the hidden layer Z (at the output of the encoder 201e and the input of the decoder 201d) is in the reduced dimensionality (latent variable or principal component) form. During training, a large number (e.g., 1,000 to 10,000) of body surface images 102 are input to the decoder 201e of the first autoencoder 201. The data from the encoder 201e are decoded by the decoder 201d, and the data from each hidden layer of the decoder 201d are back propagated to the encoder 201e. After processing sufficient training samples, the difference between the output X' and input X is smaller than a threshold value, and the encoder 201e provides the latent variables or principal components 102' representing the body surface.

A second autoencoder 202 has an encoder 202e and a decoder 202d. The second autoencoder 202 can have a design similar to, or different from, the first autoencoder 201. Even if the second autoencoder 202 has a similar design to the first autoencoder 201, the coefficient array in the second autoencoder 202 is likely to be different from the coefficient array of the first autoencoder 201. During training, a large number (e.g., 1,000 to 10,000) of organ surface images 104 are input to the decoder 202e of the second autoencoder 202. The training dataset of organ surface data 104 can correspond to a same or different set of patients from the training dataset of body surface data 102. The organs can be lungs, heart, liver, kidneys or brain, for example. The data from the encoder 202e are decoded by the decoder 202d, and the data from each hidden layer of the decoder 202e are back propagated. After sufficient training samples, the hidden layer Z of autoencoder 202 provides the values of the latent variables or principal components 104' representing the organ surface, and the decoder 202d of the second autoencoder is configured to predict the organ surface 104 based on the values of the latent variables or principal components 104'. Note that the manifold of the organ generally differs from the manifold of the body surface.

In some embodiments, the regressor 203 is a deep neural network (DNN). The regressor 203 is trained after both the first autoencoder 201 and the second autoencoder 202 have completed training. The regressor 203 is trained using the latent variables or principal components 102' output from the encoder 201e and the latent variables or principal components 104' output from the encoder 202e. For training the regressor 203, the training dataset should include a large number (e.g., 600 to 10,000) of sets, where each set includes body latent variables or principal component 102' and respective organ latent variables or principal component 104' corresponding to the same person. For example, if there are more body surface patient samples 102 than organ surface patient samples 104, the regressor 203 is trained using only the data from patients for whom both body surface data 102 and organ surface data 104 are available.

The regressor 203 can implement linear regression, least absolute shrinkage and selection operator (LASSO) regression (also referred to as sparse linear regression), sparse principal component analysis (PCA) regression, deep regression or other regression method. The regressor 203 determines the operator $f$ (latent body variables) which transforms the body latent variables or principal components 102' into the organ latent variables or principal components 104'. The operator $f$ (latent body variables) can be a linear or non-linear operator. The regressor 203 can determine the operator $f$ (latent body variables) which can generate the predicted organ latent variables or principal components 104' from the body latent variables or principal components 102', and provide the organ latent variables or principal components 104' to the hidden layer Z (at the input of the decoder 202d of autoencoder 202). When the regressor 203 has been sufficiently trained, the output of the operator $f$ (latent body variables), based on the body surface latent variables or principal components 102', is within a threshold value of the latent variables or principal components 104' output by the encoder 202e.

Because the regressor 203 operates on body latent variable or principal component data 102' with reduced dimensionality, the regressor 203 can process the body surface data at a faster speed using smaller arrays than another regressor (not shown) could operating on the full-dimensionality body surface data 102.

FIG. 3B shows the prediction block 119 configured for the test phase, after the first autoencoder 201, the second autoencoder 202 and the regressor 203 have been trained. The encoder 201e of the first autoencoder 201, the regressor 203, and the decoder 202d of the second autoencoder 202 are used, and are connected for processing in that order. For example, in software implemented embodiments, the output of the encoder 201e is provided to the input of regressor 203, and the output of the regressor 203 is provided to the input of the decoder 202d.

In operation, the 2.5D or 3D camera 101 captures a depth image of the body surface 102 of the patient. The depth image data 102 are input to the (trained) encoder 201e of autoencoder 201. The latent variables or principal components 102' representing the body surface are output to the regressor 203, which computes the latent variables or principal components 104' representing the organ surface. The latent variables or principal components 104' are provided to the input of the decoder 202d. The decoder 202d outputs the predicted organ surface 104 at high resolution.

Although the hidden layers of autoencoders 201 and 202 in FIGS. 3A and 3B include two encoding layers and two decoding layers, the autoencoders 201 and 202 can have any number of hidden layers appropriate for the dimensionality reduction desired.

FIGS. 4-7 summarize the training phase and test phase. As discussed above, the learning can follow a stage-wise approach.

Figure 4:
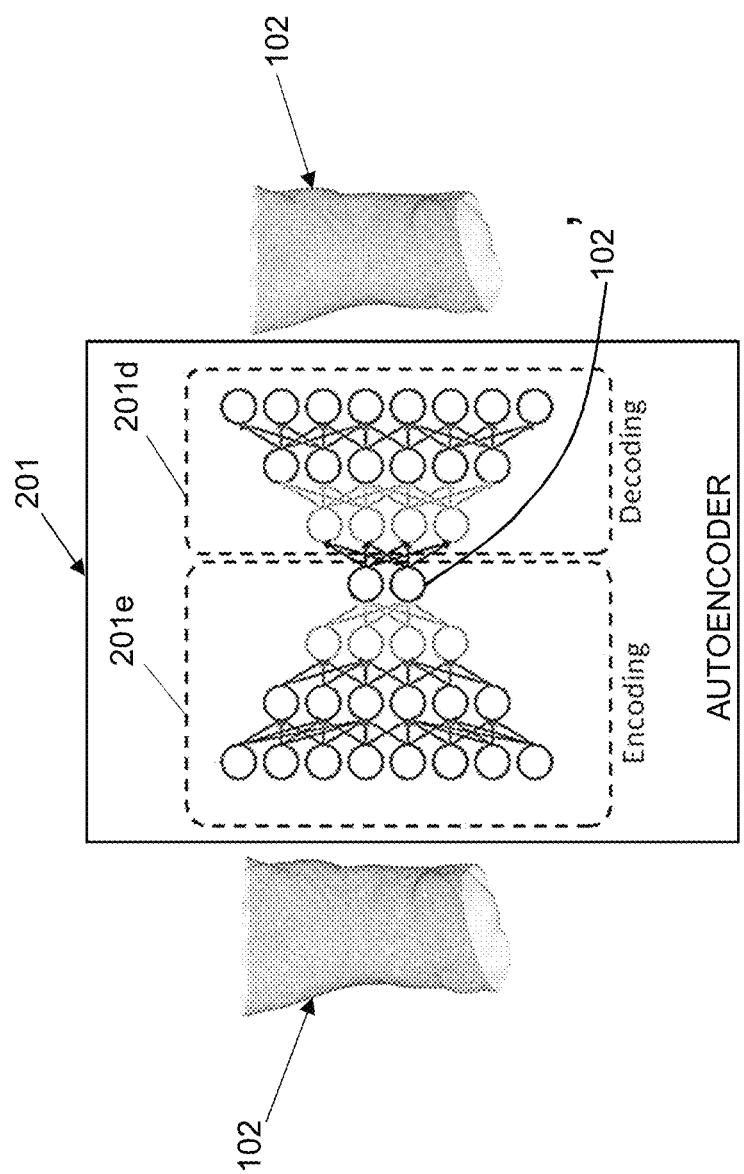
FIG. 4 shows the configuration for a first training phase, for training the first autoencoder of FIG. 3A.

FIG. 4 shows training stage 1. In stage 1, the prediction block 119 uses a first autoencoder 201 (network 1) to learn the manifold for torso points.

In FIG. 4, body surface images 102 are input to the autoencoder 201. The encoder 201e encodes the body surface images 102 and provides body latent variables or principal coordinates 102'. The decoder 201d decodes the body latent variables or principal coordinates 102' and generates body surface images 102. The hidden layer outputs are back propagated to the encoder 201e.

Figure 5:
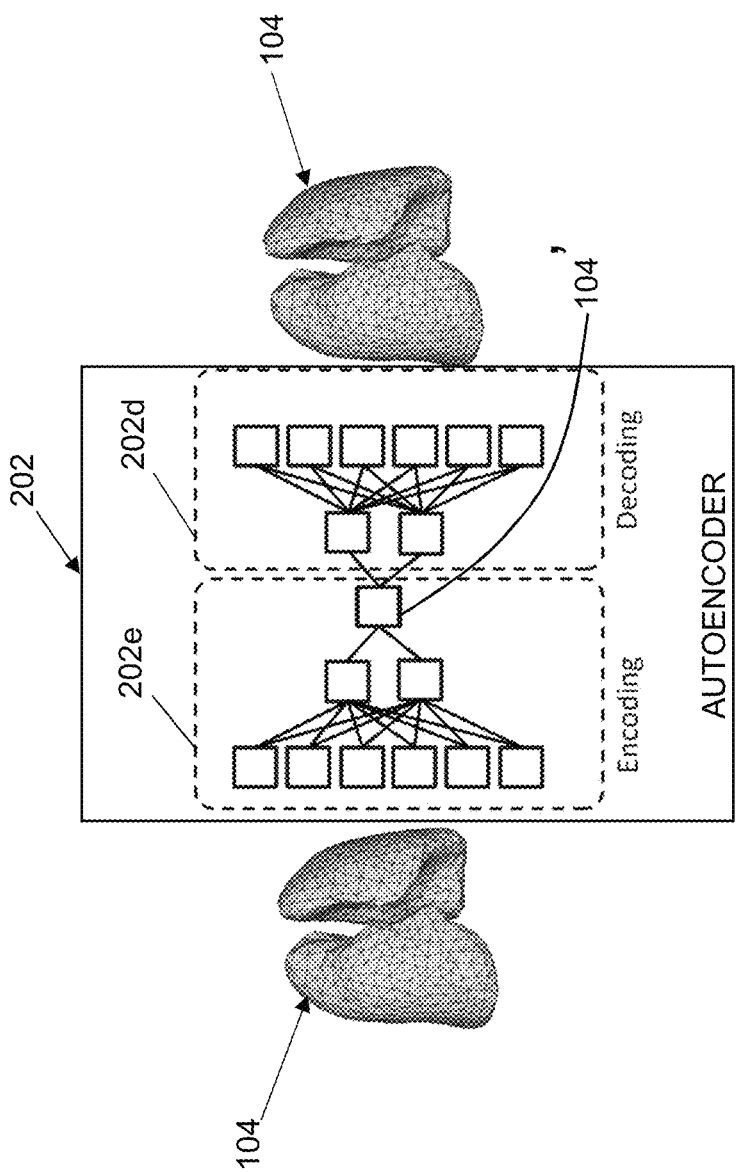
FIG. 5 shows the configuration for a second training phase, for training the second autoencoder of FIG. 3A.

FIG. 5 shows training stage 2. In stage 2, the prediction block 119 uses a second autoencoder 202 (network 2) to learn the manifold for points on an internal surface of an organ (e.g., lungs, heart, liver, kidneys or other anatomical structures of interest).

In FIG. 5, organ surface images 104 are input to the autoencoder 202. The encoder 202e encodes the organ surface images 104 and provides organ latent variables or principal coordinates 104'. The decoder 202d decodes the organ latent variables or principal coordinates 104' and generates organ surface images 104. The hidden layer outputs are back propagated to the encoder 202e.

Figure 6:
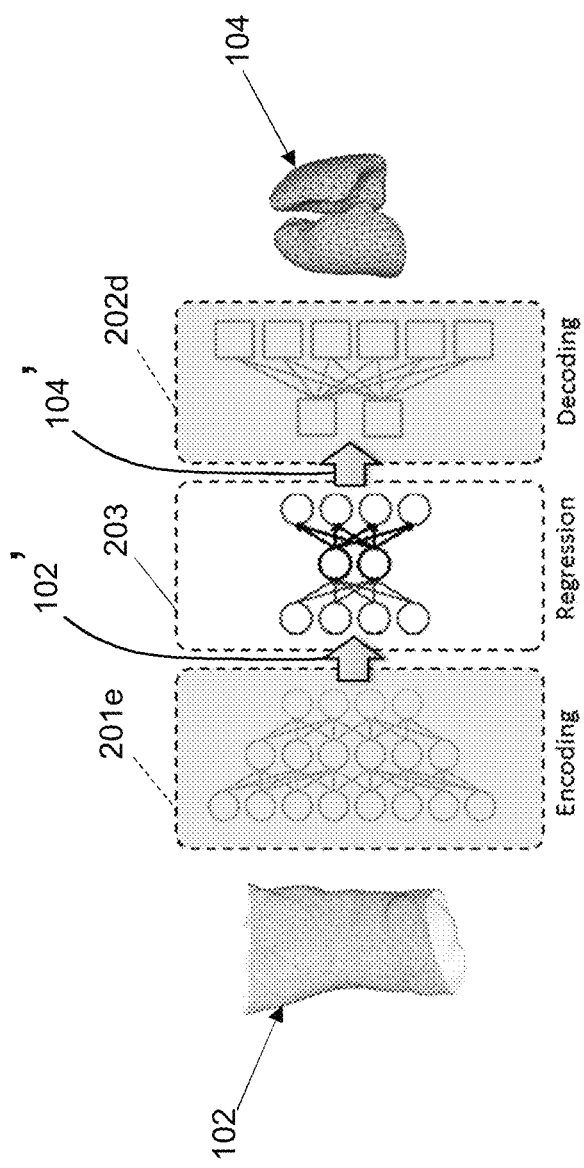
FIG. 6 shows the configuration for a third training phase, for training the regressor of FIG. 3A.

FIG. 6 shows training stage 3: In stage 3, the network of regressor 203 (network 3) learns an operator $f$ (latent body variables) for transforming the encoded torso observations 102' into encoded organ (e.g., lung, etc.) observations 104'. The same operator $f$ (latent body variables) can be used after training, for transforming encoded torso observations 102' into encoded organ (e.g., lung) predictions 104'. Note that in stage 3 (while training the regressor 203), the weights (coefficients) of the encoding network 201e of the skin surface and decoding network 202d of the organ surface are fixed, as indicated by the shading in encoder 201e and decoder 202d. This allows independent training of the autoencoder 201, regressor 203 and autoencoder 202.

In FIG. 6, the regressor 203 receives the body latent variables or principal coordinates 102' and generates organ latent variables or principal coordinates 104'. When the generated organ latent variables or principal coordinates 104' from regressor 203 differ from the organ latent variables or principal coordinates 104' from encoder 202e by less than a threshold value, the regressor 203 is sufficiently trained.

Figure 7:
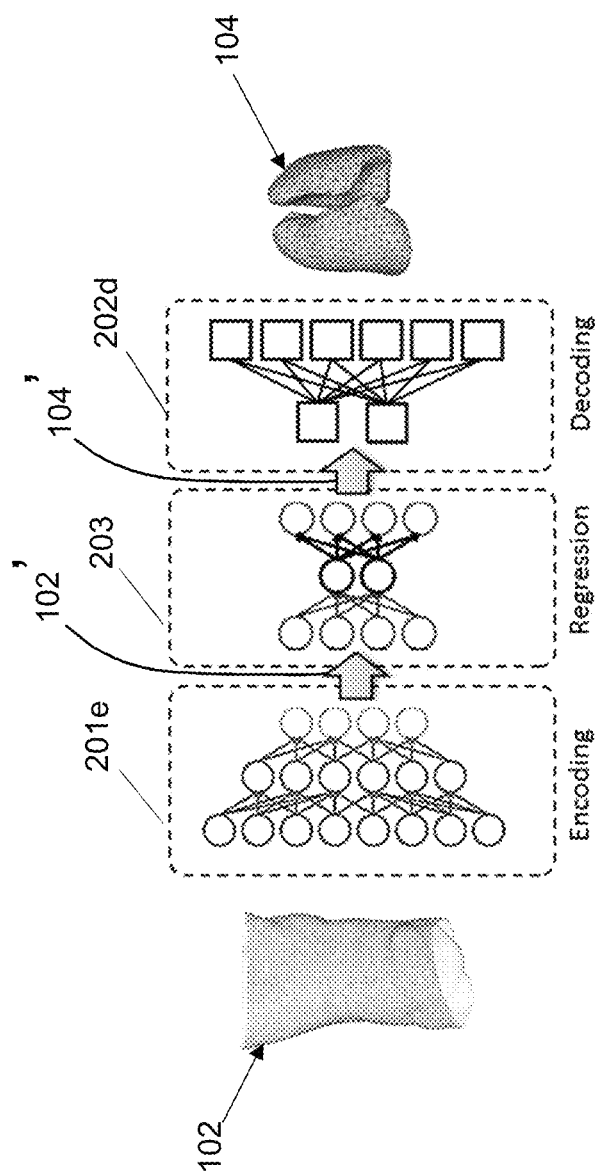
FIG. 7 shows the configuration for the test phase.

FIG. 7 shows stage 4, which is the test phase. The encoder 201e of the first autoencoder 201, the regressor 203 and the decoder 202d of the second autoencoder 202 are combined in that order. In some embodiments, the combined network 201, 203, 202 is fine-tuned with several training examples including body surface data 102 and organ surface data 104. The body surface data 102 are processed by the combined network, outputting predicted organ surface data 104. The predicted organ surface data 104 can be compared to the actual organ surface data, and the fine tuning continues until the difference between the predicted organ surface data 104 and the actual organ surface data is less than a threshold value.

In some embodiments, the fine tuning involves back propagating the error between the predicted organ surface and the actual organ surface. During back propagation, a low learning rate can be used to ensure the network weights do not diverge.

FIG. 7 shows the test phase configuration, including the encoder 201e, regressor 203 and the decoder 202d. A torso image 102 is input. The encoder 201e provides body surface latent variables or principal components 102. The regressor receives the body surface latent variables or principal components 102 and provides the organ latent variables or principal coordinates 104'. The decoder 202d receives organ latent variables or principal coordinates 104' and generates the predicted organ surface images 104.

Figure 8:
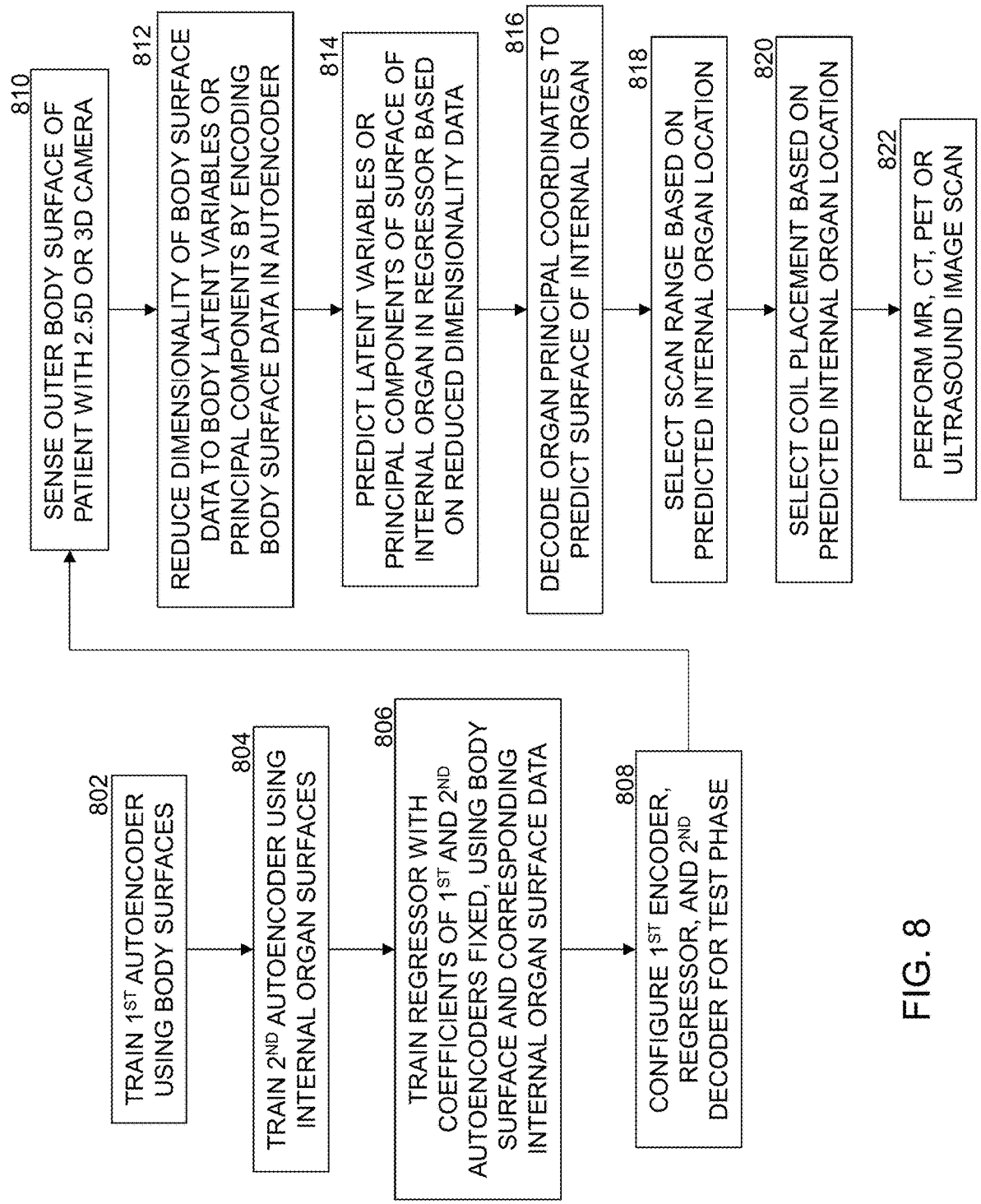
FIG. 8 is a flow chart of the method according to some embodiments.

FIG. 8 is a flow chart of a method for training and using a system 100. Steps 802-806 cover the training phase. Steps 810 to 822 cover the test phase.

At step 802, the first autoencoder 201 is trained using a first dataset of body surface training images 102. In some embodiments, a 3D avatar mesh of the subject is formed based on a 2.5D or 3D image from a depth camera 101 using a trained parametric deformable model, as disclosed in US 2015/0213646 A1, which is incorporated by reference herein in its entirety. The body surface geometry can then be defined by the 3D avatar mesh and input to the autoencoder 201. At the conclusion of training, the encoder 201e of autoencoder 201 is configured to output reduced-dimensionality (latent variable or principal coordinate) body surface data 102' corresponding to any input body surface data 102.

At step 804, the second autoencoder 202 is trained using a second set of internal organ surface training images. The training set for step 804 can correspond to the same subjects as in step 802 or different subjects from those in step 802.

At step 806, the regressor 203 is trained using a third training dataset. During training of the regressor 203, the coefficients of the first autoencoder 201 and second autoencoder 202 remain fixed. For each body surface input image data, the internal organ surface image data corresponding to the same subject are included. The third training dataset can include one or more images from the first dataset and/or one or more images from the second dataset. The third dataset can partially overlap with the first and/or second dataset. Alternatively, the third dataset can have 0% or 100% overlap with the first and/or second dataset. Body surface images without corresponding organ images are excluded from the third dataset. Similarly, organ images without corresponding body surface images are excluded from the third dataset.

At step 808, the first encoder 201e, regressor 203 and decoder 202d are configured for the test phase, so first encoder 201e provides reduced dimensionality body surface data 102' to the regressor 203, and regressor 203 provides reduced dimensionality organ surface data 104' to the second decoder 202d.

At step 810 an outer body surface test image 102 of a subject (patient) is input to the first encoder 201e.

At step 812, the first encoder 201e of the first autoencoder 201 encodes the body surface data 102 to reduce the dimensionality of the body surface data 102 to body latent variable or principal coordinate data 102' in a body surface manifold.

At step 814, the regressor 203 predicts the internal organ surface latent variables or principal components 104' (in an organ surface manifold), based on the body latent variable or principal coordinate data 102'.

At step 816, the second decoder 202d of the second autoencoder 202 decodes the internal organ surface latent variables or principal components 104' to obtain internal organ surface data 104.

At step 818, the scan range of the scanner 105 is selected, based on the predicted location of the internal organ. This allows the range of the scan to be limited to reduce the amount of radiation to which the patient is exposed and reduce the (temporal) duration of the scan.

At step 820, the coil placement for the scanner 105 is selected based on the predicted location of the internal organ. This allows the scanning sequence to be optimized for the location, shape, and size of the internal organ.

At step 822, the scanner 105 performs an MR, CT, PET, or ultrasound imaging scan, using the selected scan range and/or coil placement.

Prediction Block Architecture

The prediction block 119 and regressor 203 can have any of a variety of architectures.

Linear Regression

In some embodiments, the regressor 203 uses linear regression. Linear regression has an advantage of being computationally inexpensive. A linear regression model is a linear projector from an input vector X to an output vector y=βX+e, where β and e are constants.

Ordinary Least Squares (OLS) is employed to learn the model parameters (β) from a training dataset of $\{X_i, y_i\}^N$.

$$\hat{\beta}=(X^TX)^{-1}X^Ty=(\Sigma x_i x_i^T)^{-1}(\Sigma x_i y_i)$$

The set of the points on the organ (e.g., lung) surface can be predicted from a patient surface (avatar mesh) i.e. X=Set of avatar points on torso, y=Set of points on lung surface. In some embodiments, the estimation error (total least square error over the entire dataset) may be high, implying that the model correlating the input and output data is complex. For example, the error may be attributed to the potential noisy points in the input data and/or retention of the noisy points by the linear model.

LASSO Regression (Sparse Linear Regression)

Least absolute shrinkage and selection operator (LASSO) or sparse linear regression model is also a linear projector from input vector X to an output vector y=βX+e, but the coefficients (β) are enforced to be l1 sparse, providing enhanced computation speed.

$$\min_{\beta_0,\beta}\left\{\frac{1}{N}\sum_{i=1}^{N}(y_i - \beta_0 - x_i^T\beta)^2\right\} \text{ subject to } \sum_{j=1}^{p}|\beta_j| \le t$$

In some embodiments using LASSO regression, the estimation error (least squares over the entire dataset) may be high. The predicted points may not enforce lung like shape in all cases.

Sparse Principal Component Regression

Other embodiments perform regression on a manifold in which every point represents a valid shape in a metric space, thus enforcing the shape constraints. Instead of regressing the dependent variable y on the explanatory (independent) variables X directly, the principal components of the explanatory variables are used as regressors. Some embodiments use LASSO regression over the Principal Component Analysis (PCA) manifold; the sparsity provides additional robustness. Further, instead of performing regression over the dependent variables directly, the coefficients of the PCA manifold are predicted over the dependent variables. Using the PCA over the output space (dependent variables) also ensures that the output points are distributed on the manifold of lung shape, thus ensuring the predicted mesh is lung-like.

Instead of the PCA manifold (linear), some embodiments use other manifold learning methods that may be able to capture even finer details such as kernel PCA or Autoencoders.

Deep Regression

Some embodiments learn a deep regression model to predict the internal anatomical data 104 from surface data 102. Given the surface points or volumetric data, the system learns an encoder network (using Autoencoder 201) that projects the input torso points 102 to a torso manifold and determines latent variable values 102'. The system 100 also learns a decoder (using Autoencoders) that reconstructs the organ (e.g., lung) surface 104' from points on the organ (e.g., lung) manifold, and learns the correlation between the corresponding points on the torso manifold and the organ (e.g., lung) manifold. This architecture is presented in FIGS. 3A-7.

Figure 9A:
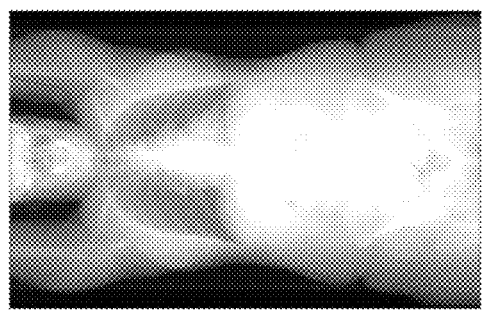
FIGS. 9A to 9C show an example of a predicted lung location using the method described herein.

Sample results obtained using the model trained using the pipeline described above are shown in FIGS. 9A-9C. FIG. 9A shows an image from an input CT scan of a patient representing the "ground truth" CT volume with all anatomical details. The CT scan included a plurality of slices parallel to the frontal or coronal plane (i.e., parallel to the plane of the page). In order to obtain the data for FIG. 9A, the plurality of slices included several slices extending from the patient's anterior skin to the posterior skin. This included exposing the patient's entire torso to radiation at a full dosage. To generate each pixel in FIG. 9A, the pixel values in each slice having the same (medial-lateral coordinate and the same superior-inferior coordinate) were averaged to create a 2D projection.

Figure 9B:
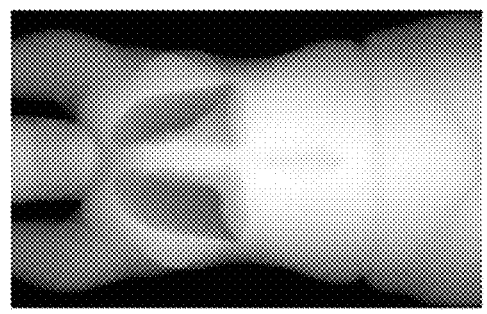

FIG. 9B is a synthetic CT image corresponding to the subject of FIG. 9A. The image of FIG. 9B was obtained by first processing the CT scan data used in FIG. 9A, to compute the skin surface and the organ (e.g., lung) surface (based on the respective slices including these two surfaces). Once the body surface and organ surface are available (using CT processing tools), the synthetic CT of FIG. 9B was generated with a body and only lung organs. Other organs and all bones were omitted. The pixels values for the same location within each slice were averaged (as in FIG. 9A, but omitting bones and other organs) to create the 2D projection shown in the FIG. 9B. The synthetic image is synthetic in that the image contains measured points and additional points generated using a parameterized deformable model (PDM).

The synthetic CT data allows the prediction block 119 to focus the regression on the body surface 102 and lung surface 104, and ignore variations in all the other tissues (such as other organs and bones). Thus, the synthetic CT image of FIG. 9B contains the types of input data 102 and 104 that are provided to the autoencoder 201 during training.

Figure 9C:
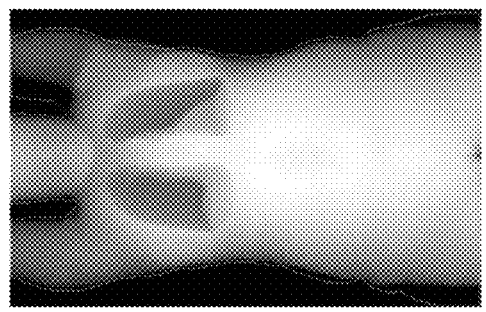

FIG. 9C is a predicted volumetric CT image generated by the prediction block 119 during the test phase. A 2.5D or 3D depth image is taken to collect body surface data 102 from the patient. The body surface data 102 are input to encoder 201e. Based on the body surface data 102, the prediction block 119 predicted the surface of the lungs as shown in FIG. 9C. The predicted location of the lungs in FIG. 9C closely matches the location of the lungs in the synthetic image of FIG. 9B. Thus, the predicted image 9C can be used to determine the scanning range for the scanner 105 and/or the locations of the coils (not shown) for collecting a CT image of the lungs without scanning the entire torso.

In some embodiments, the method is used to help plan CT dose for optimal CT scanning by predicting a synthetic CT scan from the patient body surface model obtained from 2.5D sensor.

The synthetic CT scan is optimized to model certain factors involved in dose planning, omitting other details. CT scanners regulate the X-ray dose (by modulating the current) appropriately such that dose is reduced at regions with large cavities (e.g., lungs) and high at regions where the body density is higher such as along shoulders and parts in abdomen.

Appropriately controlling the dose not only helps the patient (by reducing the dose in regions where large dose is not required) but also improves the reconstructed image quality. In some embodiments, a synthetic CT image cam have several advantages. A synthetic images is based on other information in addition to 2D projections of the 3D internal anatomy, and does not vary with different table height or have perspective artifacts. Thus, the synthetic CT image can be interpreted as a density prediction for all the voxels inside the body surface, and does not need to model fine anatomical structures such as individual soft tissues or arteries. The method can focus on regions where the body density is much higher or lower than the average.

The method can use a statistical correlation model between the detailed patient surface geometry and the internal anatomical structures (such as organs and body markers). A correlation model can be learned using machine learning from a large dataset, and given the prediction of these anatomical structures, a synthetic CT image can be obtained as described herein. Further, the synthetic CT can also be based on measurements from a scouting CT scan such as a topogram.

In some embodiments, the system can obtain a synthetic CT image using geometric measurements on the body outer surface. The synthetic CT image is a 3D image where each voxel provides an estimate of the expected material density based on a density distribution over a large dataset of patients. The synthetic CT image is not meant to be used for diagnostic but for scan planning such a patient positioning and scan dose planning. The system can refine the synthetic CT image if a scouting CT image (e.g., as a topogram or low dose coarse CT image) is available.

The density prediction may be done using statistical correlation modeling between body surface geometry and internal patient anatomy or using machine learning algorithms over a large dataset.

The system can use one of various methodologies to generate a synthetic CT image from body surface data for dose planning. For CT scanning, a higher dose generates images with higher quality compared to the images captured with low dose. However a lower dose is better for the patient's safety. The method and system described herein can be used to determine an "optimal dose" such that the image has sufficiently high quality for diagnostic purposes while exposing the patient with as low dose as practical. The methods described herein synthesize a CT image from the patient surface geometry and the scouting scan (topogram) if available.

Synthetic CT Image Generation for Dose Planning

The synthetic CT image is a 3D image similar to a CT volume, where each voxel stores the predicted or expected density based on partial measurements such as patient body geometry and/or scouting CT scan (a low dose, coarse CT image). The estimated image captures information sufficient to control the attenuation (thus radiation dose) to get homogeneous noise over the entire the entire patient. Mathematically, the synthetic CT image is formulated as a linear combination of skin mask, various organ masks as well as bone masks, as follows:

$$CT_{synth} = w_{skin}*V_{skin} + w_{lungs}*V_{lungs} + w_{pelvis}*V_{pelvis} + w_{skull}*V_{skull} + \ldots$$

Figure 10B:
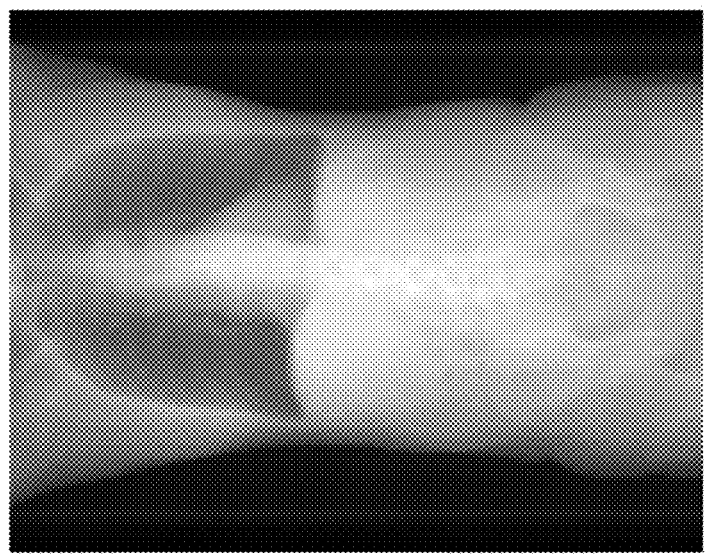
FIG. 10B shows the synthetic CT volume (coronal projection) corresponding to the sample CT volume of FIG. 10A.
Figure 10A:
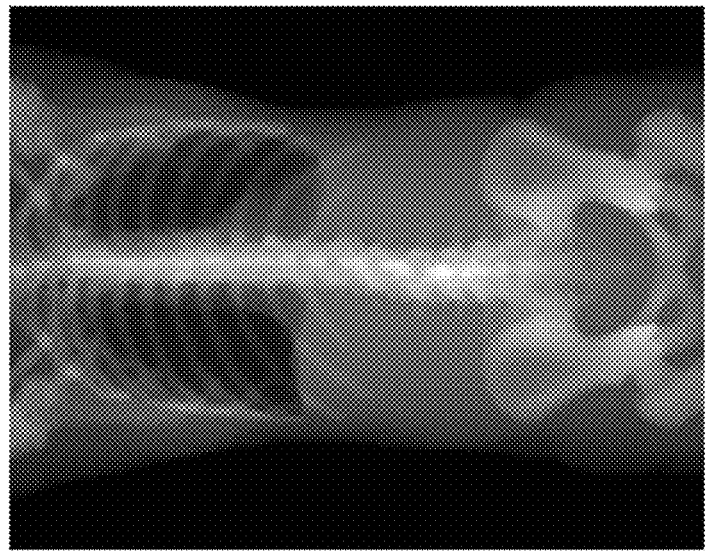
FIG. 10A shows a sample CT volume.

The weights are set based on the mean density within these body regions, which may be expressed in Hounsfield units (HU). For example, the average density within a lung region is −800 HU, and the average density of soft tissues is close to 0 HU. As discussed above, FIG. 10A shows a sample CT image and FIG. 10B shows the corresponding synthetic CT image generated by combining the skin, lung and bone masks.

Several approaches can be used to obtain the individual organ and bone masks from a patient body surface data. The patient body surface can be obtained using 2.5D sensors as described in US 2015/0213646 A1.

Regression of Internal Anatomical Surfaces to Volume

Some embodiments use regression methods to estimate the surface of internal anatomical structures from patient body surface as described above. For the purpose of CT dose planning, one can focus on the anatomical structures where the density is much higher or lower than average i.e. organs such as lungs and regions with higher bone density such as pelvis or shoulders. The methods described herein can be used to regress the organ surfaces as well as several internal body markers from surface data. Given an organ surface, this method can generate a volumetric mask which is used to represent the organ volume. The body marker data can be used to interpolate the bone masks in the regions of interest. This can be done by placing a mean bone mask in the region of interest and use non-linear deformation such as thin plate splines (TPS) to deform the bone mask to fit the predict body markers. As discussed above, FIG. 8 depicts how the regressed internal anatomical surfaces can be used to obtain a volumetric mask and combined in a synthetic CT volume.

Volumetric Regression

In another embodiment, an organ volume may be directly regressed from the skin surface volume data. Assuming a linear regressive relationship, this can be mathematically written as $$A*[\text{Body Surface Volume}] = [\text{Volume with Anatomical Structure}]$$

where A is the regression matrix, Body surface volume 1100 is a vectorized representation of the 3D volume/matrix with voxels inside the body surface marked as 1, otherwise 0. FIG. 11 is a schematic diagram showing this flow. Volume with anatomical structure 1110 is a vectorized representation of the 3D volume/matrix with voxels inside the organ or bone region as 1, otherwise 0.

For volumetric regression, the individual input and output samples are defined in fixed space; however the organs and body shape for different individuals would be different and hence a fixed normalized volume can be defined for both input and output. In one embodiment, a fixed 3D volume (in metric space) has a particular body marker as a fixed point (such as body center as volume center or neck center a volume top center).

In another embodiment, the volumes may be normalized based on multiple body markers, such that the in the normalized space the number of voxels from neck to ischium is fixed across all patients. FIGS. 12A-12C show normalized volumes for bone masks defined over the thorax+abdomen region. In FIGS. 12A-12C, the individual volumes are cropped to be of equal size. Each voxel is 1 mm×1 mm×1 mm. On one hand, this space is the key region within the field of view for all patients; on the other hand, this space normalizes all volumes to the same height, making it more difficult for the regressor to learn scale related deviations.

Although the linear regressive model is described above, in alternative embodiments, its PCA variants may be used. Other alternative embodiments can model the complex dependency between the input and output variables. Thus, non-linear projection manifold learning technique such as kernel PCA or deep manifold learning may be used to ensure the generated masks are physically achievable.

Topogram Based Refinement

While the synthetic CT image has the benefit of minimizing the dose, alternative embodiments can achieve greater accuracy. Some alternative embodiments refine the synthetic CT image with a CT scout scan. A CT scout scan may be a topogram image or a very low dose volumetric image which can be used for scan planning of a more detailed CT scan. The following example uses a topogram image, but the presented technique can also be applied to other scouting scans as well.

Given a topogram image, the patient skin surface boundaries, boundaries of the anatomical structures, and body markers (such as lung center etc.) can be detected in 2D. Such an approach may not have correct image perspective due to the cone beam acquisition apparatus. While the body marker estimates obtained from regression can be directly updated to match the topogram measurement (since these are point observations), the boundary (line) measurements may be difficult to incorporate into the 3D synthetic CT image. An approach based on space carving methods can deform the initial CT shape to fit the topogram measurements. FIG. 13A shows an example of this approach. FIG. 13B shows a detailed example of the method in FIG. 13A.

The synthetic CT image only shows skin surface, lungs and bones. Some embodiments refine the skin surface, lungs and bones and ignore all other anatomical details in the topogram image. Assume that several key landmarks as well as organ and bone boundaries are also provided as input, and can be used. However, in practice, such information can be obtained by applying a deep network to process the topogram image.

Some embodiments apply a deep network to detect key landmarks in the topogram image. Some embodiments apply a deep network for segmenting the topogram image by labelling each pixel to belong. to one of the following four classes—background, body (inside patient's body), lung or bone.

FIG. 13A shows a method using a neural network. Given this landmark information, step 1301 performs an affine transform based on markers and boundaries. The affine transform preserves ratios of distances between points lying on a straight line (but may not preserve angles between lines or distances between points).

At step 1303, the hull estimation is performed, to estimate a 3D volume from the 2D surfaces of skin and lungs.

At step 1305, voxels that deviate substantially from the hull volume are "carved out". The carved out voxels can be replaced by interpolation between the voxels surrounding the "carved out" voxel, for example.

FIG. 13B is a more detailed example of a deep neural network embodiment.

Step 1302 first applies an affine transform to the predicted volume based on the landmarks and 3D bounding box.

Step 1304 performs slice-by-slice affine scaling using delineation.

Step 1306 uses the 2D segmentation of skin and lungs to create a 3D volume by extruding the 2D mask based on the projection parameters. This volume is referred to as the "perspective hull volume".

Step 1308 performs volume carving by carving out all voxels in the synthetic CT that are not consistent with the perspective hull volume generated from the skin mask or the lung mask.

FIGS. 14A-14A-14C show comparisons between an original CT image and the synthetic CT results obtained using volumetric regression (lungs and bones) as well as results after refinement using the topogram image. FIG. 14A shows the CT topogram, FIG. 14B shows the synthetic CT as predicted only from the surface data without internal CT data. FIG. 14C shows the synthetic CT after refinement using the topogram.

Although an example is shown for predicting the location of the lungs, the method and system can be used to predict the location of other organs. For example, the prediction block 119 can be trained to predict the location of the patient's kidney. The second autoencoder 202 can be trained using images of kidneys, and the regressor 203 can learn to predict the location of the kidney surface in latent variables or principal coordinates 104', based on the compact representation (latent variables or principal coordinates 102') of the body surface 102.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method for controlling a scanner, comprising
sensing an outer surface of a body of a subject, the sensing providing body surface data comprising a skin surface of the subject;
using a machine-trained predictor to predict a surface of an internal organ of the subject based on the body surface data, the machine-trained predictor including a regressor that receives as input to the regressor a representation of the skin surface and outputs, in response to the input and by the regressor, a representation of the surface predicted as a mesh or volume mask output by the machine-trained predictor, wherein the predicting includes:
encoding the body surface data into body surface principal coordinates;
predicting a set of organ principal coordinates representing the surface of the internal organ; and
decoding the set of organ principal coordinates to predict the surface of the internal organ, wherein the encoding is performed by a first autoencoder, predicting the set of organ principal coordinates is performed by Hall the regressor, and the decoding is performed by a second autoencoder, the method further comprising, before the sensing:
training the first autoencoder using a first plurality of body surfaces;
training the second autoencoder using a first plurality of organ surfaces; and
training the regressor using a plurality of body-surface, organ-surface sets, each body-surface, organ-surface set including a plurality of body-surface latent variable values and a plurality of organ-surface latent variable values corresponding to the body-surface latent variable values; and controlling the scanner based on the predicted surface of the internal organ, the scanner controlled for scan range or coil placement.

2. The method of claim 1, wherein using the machine-trained predictor to predict the surface includes:
reducing dimensionality of the body surface data;
predicting a compact representation of the surface of the internal organ based on the reduced dimensionality body surface data; and
expanding the compact representation.

3. The method of claim 2, wherein the regressor is a sparse linear regressor.

4. The method of claim 2, wherein the regressor is a least absolute shrinkage and selection operator (LASSO) regressor.

5. The method of claim 2, wherein the regressor is a deep neural network.

6. The method of claim 1, wherein the scanner is a magnetic resonance (MR) scanner, and the controlling includes selecting the coil placements of a plurality of coils of the MR scanner.

7. The method of claim 1, wherein the scanner is a computed tomography (CT) scanner, and the controlling includes selecting the scan range of the CT scanner.

8. A method for controlling a scanner, comprising
sensing an outer surface of a body of a subject, the sensing providing body surface data comprising a skin surface of the subject;
using a machine-trained predictor to predict a surface of an internal organ of the subject based on the body surface data, wherein using the machine-trained predictor to predict the surface includes: reducing dimensionality of the body surface data by a machine-trained encoder of the machine-trained predictor, predicting a compact representation of the surface of the internal organ as output of a machine-trained regressor in response to input to the machine-trained regressor of the reduced dimensionality body surface data, and expanding the compact representation by a machine-trained decoder of the machine-trained predictor, wherein the predicting includes:
encoding the body surface data into body surface principal coordinates;
predicting a set of organ principal coordinates representing the surface of the internal organ; and
decoding the set of organ principal coordinates to predict the surface of the internal organ, wherein the encoding is performed by a first autoencoder as the machine-trained encoder, predicting the set of organ principal coordinates is performed by the machine-trained regressor, and the decoding is performed by a second autoencoder, the method further comprising, before the sensing:
training the first autoencoder using a first plurality of body surfaces;
training the second autoencoder using a first plurality of organ surfaces; and
training the regressor using a plurality of body-surface, organ-surface sets, each body-surface, organ-surface set including a plurality of body-surface latent variable values and a plurality of organ-surface latent variable values corresponding to the body-surface latent variable values; and
controlling the scanner based on the predicted surface of the internal organ.

9. A method for controlling a scanner, comprising
sensing an outer surface of a body of a subject, the sensing providing body surface data comprising a skin surface of the subject;
using a machine-trained model to predict a surface of an internal organ of the subject based on the body surface data, wherein the predicting includes encoding the body surface data into body surface principal coordinates by a first machine-trained autoencoder, predicting a set of organ principal coordinates representing the surface of the internal organ as an output by a machine-trained correlator in response to input of the body surface principal coordinates to the machine-trained correlator, and decoding the set of organ principal coordinates to predict the surface of the internal organ by a second machine-trained autoencoder, the first autoencoder having been trained using a first plurality of body surfaces, the second autoencoder having been trained using a first plurality of organ surfaces, and the machine-trained correlator having been trained using a plurality of body-surface, organ-surface sets, each body-surface, organ-surface set including a plurality of body-surface latent variable values and a plurality of organ-surface latent variable values corresponding to the body-surface latent variable values; and
controlling the scanner based on the predicted surface of the internal organ.

10. The method of claim 9 wherein using the machine-trained model to predict the surface includes: reducing dimensionality of the body surface data, predicting a compact representation of the surface of the internal organ based on the reduced dimensionality body surface data, and expanding the compact representation.

* * * * *